(12) United States Patent
Lindberg et al.

(10) Patent No.: US 7,266,403 B2
(45) Date of Patent: Sep. 4, 2007

(54) METHOD AND DEVICE FOR TREATING A PROTEIN DEFICIENCY

(75) Inventors: Lars Lindberg, Barsebäck (SE); Georgios Psaros, Tullinge (SE); Göran Rydgren, Bunkeflostrand (SE)

(73) Assignee: Maquet Critical Care AB, Solna (SE)

( * ) Notice: Subject to any disclaimer, the term of this patent is extended or adjusted under 35 U.S.C. 154(b) by 411 days.

(21) Appl. No.: 10/725,303

(22) Filed: Dec. 1, 2003

(65) Prior Publication Data

US 2004/0192604 A1    Sep. 30, 2004

(30) Foreign Application Priority Data

Dec. 4, 2002    (SE)    .................................... 0203591

(51) Int. Cl.
*A61B 5/02*    (2006.01)
*A61B 5/05*    (2006.01)

(52) U.S. Cl. ...................................... 600/345; 600/529
(58) Field of Classification Search .................. None
See application file for complete search history.

(56) References Cited

U.S. PATENT DOCUMENTS

| | | | |
|---|---|---|---|
| 4,659,805 A | 4/1987 | Schilling, Jr. et al. | |
| 5,302,581 A | 4/1994 | Sarin et al. | |
| 5,670,328 A | 9/1997 | Inoue et al. | |
| 6,010,912 A | 1/2000 | Davies | |
| 6,020,307 A | 2/2000 | Egan et al. | |
| 6,308,705 B1 * | 10/2001 | Rupprecht et al. | 128/204.18 |
| 6,660,833 B1 * | 12/2003 | Walther et al. | 530/324 |
| 6,737,243 B1 * | 5/2004 | Ise et al. | 435/7.92 |

FOREIGN PATENT DOCUMENTS

| | | |
|---|---|---|
| EP | 0 511 011 | 4/1992 |
| GB | 2 259 455 | 3/1993 |
| WO | WO90/11768 | 10/1990 |
| WO | WO91/00871 | 1/1991 |
| WO | WO 00/05585 | 2/2000 |

(Continued)

OTHER PUBLICATIONS

"An ELISA Technique for Quantification of Surfactant Apoprotein (SP)-C in Bronchoalveolar Lavage Fluid," Schmidt eta l, Am. J. Respir. Crit. Care Med., vol. 165 (2002), pp. 470-474.

(Continued)

*Primary Examiner*—Charles A. Marmor
*Assistant Examiner*—Robert L. Nasser
(74) *Attorney, Agent, or Firm*—Schiff Hardin LLP

(57) ABSTRACT

In a method and device for preparation of a medicament for the treatment of lungs having a surfactant deficiency, a sample from a patient is quantitatively analyzed with regard to at least one of the proteins SP-A, SP-B, SP-C and SP-D, a determination is made as to whether a deficiency of one of the analyzed protein SP-A, SP-B, SP-C or SP-D exists and if that is the case, a determination is made of a therapeutically effective dose of a replacement substance for the analyzed protein SP-A, SP-B, SP-C or SP-D, and a medicament containing the therapeutically effective dose of the replacement substance is prepared.

5 Claims, 2 Drawing Sheets

FOREIGN PATENT DOCUMENTS

| WO | WO 00/43026 | 7/2000 |
|----|-------------|--------|
| WO | WO 01/19392 | 3/2001 |
| WO | WO 01/80633 | 11/2001 |

OTHER PUBLICATIONS

"Surfactant Protein-A in Lung Lavage Fluid Obtained from Patients with Idiopathic Pulumonary Fibrosis," Behera et al, JAPI, vol. 50 (Nov. 2002), pp. 1409-1412.

"Surfactant with SP-b and SP-C Analogues Improves Lung Function in Surfactant-Deficient Rats," Walther et al, Biology of the Neonate, vol. 82 (2002), pp. 181-187"Altered Stability of Pulmonary Surfactant in SP-C-Deficient Mice," Glasser et al, PNAS, vol. 98, No. 11 (2001), pp. 6366-6371.

"Surfactant Proteins as Genetic Determinants of Multifactorial Pulmonary Diseases," Haataja et al, Anals of Medicine, vol. 34 (2002), pp. 324-333.

"Surfactant Protein A, Phosphatidylcholine, and Surfactant Inhibitors in Epithelial Lining Fluid," Hallman et al, An. R. of Resp. Disease, vol. 44 No. 6 (1991), pp. 1376-1384.

"Determination of the Pulmonary Surfactant-Associated Protein SP-B in Amniotic Fluid with a Competition ELISA," Dilger et al, Gyn. And Obst. Invest., vol. 38, No. 1 (1994), pp. 24-27.

\* cited by examiner

METHOD AND DEVICE FOR TREATING A PROTEIN DEFICIENCY

BACKGROUND OF THE INVENTION

1. Field of the Invention

The present invention relates to a method of preparation for a medicament to treat a protein deficiency and to a medical device for treating a protein deficiency.

2. Description of the Prior Art

A substance known as surfactant is found in healthy lungs. An essential function performed by surfactant is the reduction of surface tension so that all of the alveoli can be kept open. Surfactant contains a number of proteins, the individual functions of which are not entirely understood. The main constituents, however, are known and include four different proteins: These proteins are usually named SP-A, SP-B, SP-C, and SP-D.

Different types of lung trauma influence the occurrence of surfactant, such as by a reduction in the total amount of surfactant (the creation of surfactant in the lungs is influenced) and in part by a change in the occurrence of one or more of the main proteins SP-A, SP B, SP-C, and SP-D. The consequence of the change in the occurrence of surfactant is in most cases a stiffer (less pliant) lung, often with an unknown number of alveoli that have collapsed. Gas exchange is quickly worsened as a result and the patient risks becoming dependent on mechanical ventilation in order to survive.

A more complete background description of the role played by surfactant and the physiological interplay is provided in U.S. Pat. No. 6,020,307.

An obvious treatment of surfactant deficiency is to supply exogenous surfactant, however this is not entirely without consequence. A completely synthetic surfactant is presently unavailable. Natural surfactant is manufactured from animal lungs but is expensive. The price of natural surfactant is in the region of €200 per milliliter (ml). The recommended dosage is 1.25 ml per kilogram bodyweight. For a child weighing 2 kg the cost of one dose is circa €500 but for an adult of 60 kg the cost of a dose is closer to €15,000. Dosing normally needs repeating several times during a treatment. Natural surfactant therefore cannot be used as a general treatment method, at least not for adult patients. At the same time it is true that a portion of the exogenous surfactant is forced from the lungs during expiration. This is at least in part due to the change in alveolar volume during expiration.

Although analysis methods are known to distinguish between the different proteins it is not possible to undertake continual or frequent analysis of the condition for every single patient. This is primarily because samples of surfactant are extracted from the lungs using bronchial washes or mucous suction. Both of these methods normally involve the discontinuation of the mechanical ventilation of the patient and in the worst case the patient must be disconnected from the ventilator.

There therefore exists a desire to improve the management of surfactant deficiency. A first goal is to provide more effective procedures that make possible less expensive and more effective treatment. A second goal is better and more effective sample taking that can be carried out relatively continuously. A third goal is a better and more effective means for the dosing of surfactant.

SUMMARY OF THE INVENTION

An object of the present invention is to provide a method and device for use in management of surfactant deficiency that address the problems and goals that are stated above.

The above object is achieved in accordance with the principles of the present invention in a method for preparing a medicament to treat a protein deficiency including the steps of obtaining a sample for the airways of a patient and automatically quantitatively analyzing the sample to determine a content of at least one of the proteins SP-A, SP-B, SP-C and SP-D therein, automatically determining, from the analysis of the sample, if a deficiency of one or more of the analyzed proteins exists and, if such a deficiency is determined to exist, automatically determining a therapeutically effective dose of a replacement substance for the deficient protein or proteins, and automatically preparing a medicament containing the therapeutically effective dose of the replacement substance.

As used herein, "automatically" means that the step itself is performed without human intervention, but does not preclude the possibility of a certain degree of human supervision from step-to-step.

By performing a quantitative analysis of a sample, for example with respect to the protein SP-B, the actual deficiency of this protein is established. It is then only necessary to determine a dosage that is sufficient to compensate the established deficiency. The dose is thus specific for the actual deficiency.

In principle all the proteins may be analyzed in an equivalent manner. For example, an analysis may indicate that there exists a deficiency of SP-B and SP-C only. The dosing can then be adapted after this. In this way an unnecessarily large supply of other proteins can be avoided.

The above object also is achieved in accordance with the principles of the present invention in a medical device having an analysis unit adapted to receive a sample from the airways of a patient, the analysis unit automatically undertaking a quantitative analysis of the sample to determine a content therein of at least one of the proteins SP-A, SP-B, SP-C and SP-D, and wherein the analysis unit includes a calculation unit that, from the quantitative analysis, automatically determines whether a deficiency of one or more of the proteins exists in the sample.

As used herein, "deficiency" means a deviation from a normal amount of the protein in question in the subject (animal or human). The term "normal amount" is predetermined, and can either be obtained from an earlier examination of the specific subject in question, or an amount that is normal for the relevant statistical population of subjects comparable to the subject in question.

The analysis unit is designed to analyze a test sample with regard to the existence of at least one of the proteins SP-A, SP-B, SP-C and SP-D. The test sample may be transported to the analysis unit in a number of different ways, but it is advantageous if the analysis occurs in direct connection to the test sample that has been taken from the patient. For example the analysis unit can be connected to a suction device for the suction of mucous and such from the trachea.

A fluid filled cuff having a permeable membrane is described in a co-pending United States patent application filed simultaneously herewith and having Attorney Docket No. P03,0559 ("Tracheal Insert Allowing Passage of a Selected Substance," Lindberg et al.). The membrane is designed to allow the protein (or proteins) to be analyzed to pass therethrough. The cuff may and the analysis unit may be coupled together.

From the analysis a calculation unit can determine if a protein deficiency exists and how large the dose of the protein (or an equivalent substance) should be in order to counter the deficiency. It is an advantage for this purpose if the body mass of the patient is known.

A dosing unit produces a suitable dose of the protein or proteins. The dosing unit can include reservoirs for each protein to be added and, depending on the analysis of deficiency of protein, can add a therapeutically efficient dose to the respiratory organs.

The dose may be supplied to the breathing system via a suitable patient connection (tracheal tube or tracheotomy tube) or via a separate tube that is adapted for insertion into the trachea. Such a separate tube alternatively may be fed down through an existing tube, devised as a separate channel in an existing tube, or be adapted to be connected with an existing tube. The tube may be provided with a spray nozzle in order to increase the effectiveness of the delivery.

Likewise, a direct supply via the tube should be coordinated with the breathing cycles, i.e., the supply should be done so as to achieve the greatest benefit, for example at some time from the end phase of expiration to the beginning of inspiration (in order to most effectively reduce the surface tension in the alveoli and facilitate inflation of the alveoli).

The cuff mentioned above can be employed to dose proteins through the permeable membrane.

DESCRIPTION OF THE PREFERRED EMBODIMENTS

Figure 1:
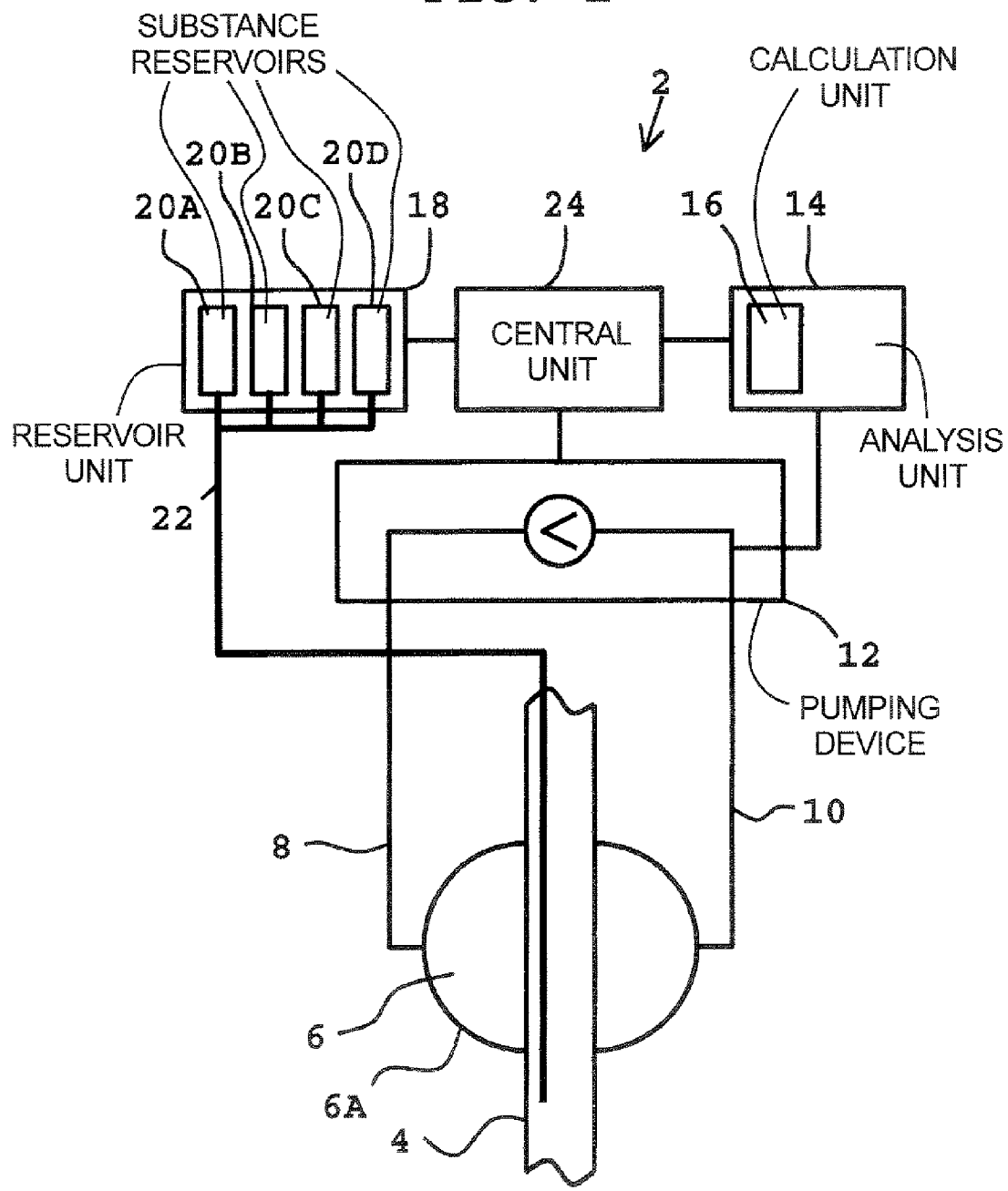
FIG. 1 shows an embodiment of a medical device according to the invention.

An embodiment of a medical device 2 according to the invention is shown in FIG. 1. The medical device 2 may include or be connected to a tube 4, preferably a tracheal tube. The tube 4 is to be dimensioned for location in the trachea of a patient (not shown). "Patient" means both animals and humans.

A cuff 6 is located on the tube 4. The cuff 6, in the present embodiment, is designed to be located below a conventional cuff. Alternatively, the cuff 6 may be formed to locate the tube 4 in the trachea and to seal the gap between the tube 4 and the trachea.

A first tube 8 conducts fluid down to the cuff 6 and a second tube 10 conducts fluid from the cuff 6. The fluid may be circulated at a known rate by a pumping device 12. The pumping device 12 may include a reservoir (not shown) for the fluid.

It is obviously not essential that the fluid be re-circulated to the cuff 6. New fluid may be supplied the whole time. This, however, results in a larger fluid usage.

In the present embodiment the entire outward facing surface of the cuff 6 is formed of a permeable membrane 6A. In order to achieve the intended effect it is, however, sufficient for only a portion of the surface, to be formed of a permeable membrane. The membrane 6A is selectively permeable to one or more of the main proteins in the surfactant, designated as SP-A, SP-B, SP-C and SP-D.

Mucous and fluids will collect around the cuff 6 and if any of the proteins SP-A, SP-B, SP-C and SP-D are present externally of the cuff 6, the partial pressures will cause the proteins to pass through the membrane 6A into the fluid in the cuff 6. Protein-containing fluid then flows through the second tube 10.

The fluid is analyzed in an analysis unit 14, connected to the pumping device 12, in order to qualitatively and quantitatively determine the level of the respective protein.

There exist many known measurement techniques for the determination of the presence of the different proteins. Antibodies, selectively chosen for a particular protein, are common and may be used on nano-spheres that flow with the fluid. The presence of the proteins may then be determined by fluorescence means of an appropriate light source within the analysis unit 14.

If desired, the nano-spheres can be marked with different color substances dependent on the selected antibody and thereby permit a simultaneous measurement and analysis of all the desired proteins.

The determination of whether there is a deficiency of protein (and in that case the extent of the deficiency) is carried out in a calculation unit 16 in the analysis unit 14.

When it has been established that one or more of the proteins SP-A, SP-B, SP-C and SP-D is/are not present in a sufficient amount a therapeutically effective dose of this/these protein(s) can be determined and dosed to the patient from a dosing unit 18. In the present example this is achieved via a dosing tube 22 to the patient's trachea and further down to the lungs.

The dosing unit 18 has a first reservoir 20A for SP-A, a second reservoir 20B for SP-B a third reservoir 20C for SP-C and a fourth reservoir 20D for SP-D. The determined doses of the proteins SP-A, SP-B, SP-C and SP-D can be dosed from respective reservoirs 20A-D via the dosing tube 22 to the patient.

A user interface, internal communications within the device, regulation and monitoring and other functions that can be provided, included in a central unit 24.

If required, a cleansing suction of the mucous can be done in a known manner (after sufficient analysis material has been collected). This also results in a better turnover of the fluids (mucous, etc) that carries with them the proteins from the lungs.

As an alternative to the conventional suction (via the tube 4) the cuff may be provided with a permanent suction feed-through that regularly suctions the mucous that lies closest to the cuff 6 (dependent on the diffusion rate across the membrane etc.).

Figure 2:
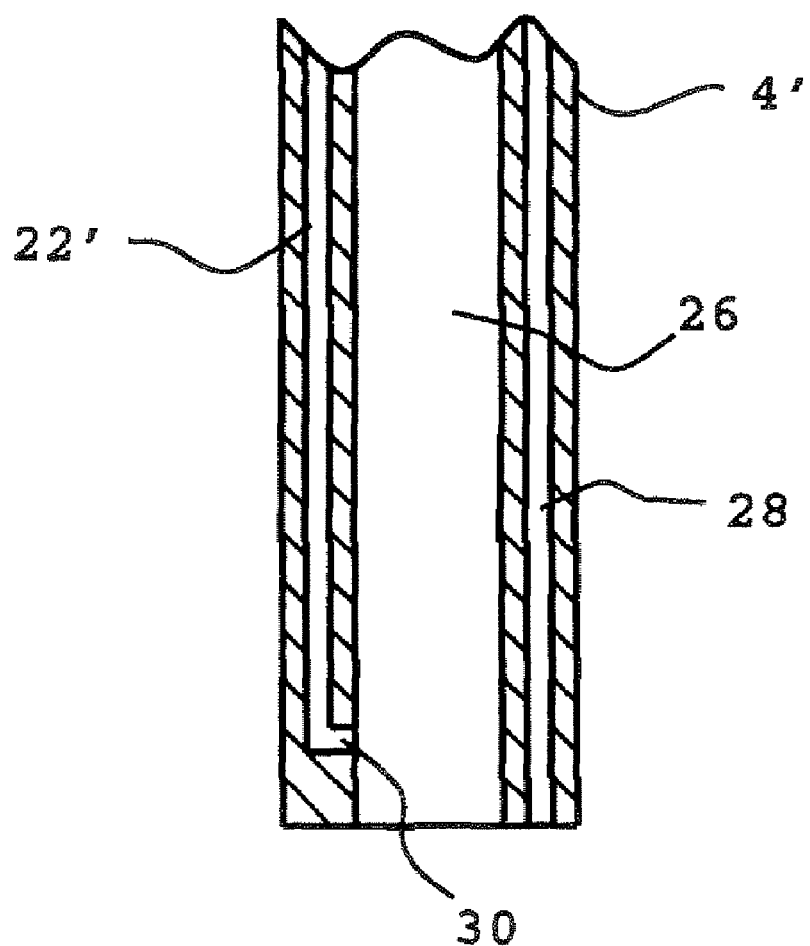
FIG. 2 shows an alternative arrangement of a tube.

An alternative design of a tube 4' with a dosing tube 22' is illustrated in FIG. 2. An air channel 26 and a sampling tube 28 are provided in the tube 4'.

Breathing gas passes through the air channel 26 during inspiration and expiration. An effective dosing of the protein (proteins) is achieved by terminating the dosing tube 22' in the air channel 26 with a spray nozzle 30. The effectiveness increases if the dosing is coordinated with the provision of breathing gas through the air channel.

The sampling tube 28 is shown as an example of that the collection of mucous and such for analysis can be done through a separate channel instead of via the cuff in FIG. 1. Naturally, it is also possible to exploit conventional suction methods in order to collect a test sample.

Combinations of the two embodiments are possible.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical device adapted for interaction with a subject to obtain a sample from airways of the subject, said medical device comprising:
   an analysis unit for automatically quantitatively analyzing said sample with regard to a content in the sample of at least one protein selected from the group of proteins consisting of SP-A, SP-B, SP-C and SP-D;
   said analysis unit including a calculation unit that, from the quantitative analysis of the sample, automatically determines whether any protein in said group of proteins is deficient in said sample; and
   a dosing unit connected to said analysis unit for automatically producing and dosing a medicament having a therapeutically effective dose of a replacement substance for remedying any deficiency of any protein in said group of proteins determined by said calculation unit.

2. A medical device as claimed in claim 1 wherein said dosing unit comprises at least one reservoir containing said replacement substance.

3. A medical device as claimed in claim 1 comprising a delivery arrangement connected to said dosing unit and adapted for interaction with the airways of the subject to deliver said medicament to the subject.

4. A medical device as claimed in claim 3 wherein said delivery arrangement comprises a dosing tube adapted for insertion into the trachea of the subject.

5. A medical device as claimed in claim 1 wherein said replacement substance comprises a substance selected from said group of proteins consisting of SP-A, SP-B, SP-C and SP-D.

* * * * *